United States Patent
Golobish et al.

(10) Patent No.: US 11,020,521 B2
(45) Date of Patent: Jun. 1, 2021

(54) HEMOCOMPATIBILITY MODIFIERS FOR CROSS-LINKED POLYMERIC MATERIAL

(71) Applicant: CytoSorbents Corporation, Monmouth Junction, NJ (US)

(72) Inventors: Thomas D. Golobish, Princeton, NJ (US); Vincent J. Capponi, Lawrenceville, NJ (US); David R. Clay, West Orange, NJ (US)

(73) Assignee: CYTOSORBENTS CORPORATION, Monmouth Junction, NJ (US)

( * ) Notice: Subject to any disclaimer, the term of this patent is extended or adjusted under 35 U.S.C. 154(b) by 0 days.

(21) Appl. No.: 16/851,305

(22) Filed: Apr. 17, 2020

(65) Prior Publication Data

US 2020/0246532 A1    Aug. 6, 2020

Related U.S. Application Data

(63) Continuation of application No. 14/230,108, filed on Mar. 31, 2014.

(60) Provisional application No. 61/806,990, filed on Apr. 1, 2013.

(51) Int. Cl.
| | |
|---|---|
| *A61M 1/36* | (2006.01) |
| *A61M 1/34* | (2006.01) |
| *A61M 1/02* | (2006.01) |
| *B01J 20/28* | (2006.01) |
| *B01J 20/32* | (2006.01) |
| *A01N 1/02* | (2006.01) |
| *B01J 20/26* | (2006.01) |

(52) U.S. Cl.
CPC .......... *A61M 1/3679* (2013.01); *A01N 1/02* (2013.01); *A01N 1/0215* (2013.01); *A61M 1/0272* (2013.01); *A61M 1/34* (2013.01); *A61M 1/36* (2013.01); *B01J 20/261* (2013.01); *B01J 20/267* (2013.01); *B01J 20/28069* (2013.01); *B01J 20/28078* (2013.01); *B01J 20/28092* (2013.01); *B01J 20/3208* (2013.01); *B01J 20/3246* (2013.01); *B01J 20/3248* (2013.01); *B01J 20/3251* (2013.01); *B01J 20/3272* (2013.01); *B01J 20/3282* (2013.01); *B01J 20/3285* (2013.01); *B01J 2220/62* (2013.01)

(58) Field of Classification Search
CPC ..... A61M 1/3679; A61M 1/0272; A61M 1/34
See application file for complete search history.

(56) References Cited

U.S. PATENT DOCUMENTS

| | | |
|---|---|---|
| 2007/0077555 A1 | 4/2007 | Nowak et al. |
| 2010/0152708 A1 | 6/2010 | Li et al. |
| 2011/0070424 A1 | 3/2011 | Young et al. |
| 2011/0282005 A1 | 11/2011 | Jiang et al. |
| 2011/0305872 A1 | 12/2011 | Jun et al. |
| 2013/0011824 A1 | 1/2013 | Chan et al. |

FOREIGN PATENT DOCUMENTS

| | | |
|---|---|---|
| CN | 101307149 A | 11/2008 |
| CN | 102307955 A | 1/2012 |
| JP | 2006-501449 A | 1/2006 |
| JP | 2006-192271 A | 7/2006 |
| JP | 2009-508542 A | 3/2009 |
| JP | 2012-510880 A | 5/2012 |
| WO | WO 2004/029221 A2 | 4/2004 |
| WO | WO 2007/024393 A2 | 3/2007 |
| WO | WO 2010/065960 A2 | 6/2010 |
| WO | WO 2012/094565 A1 | 7/2012 |
| WO | WO 2014/165421 A1 | 10/2014 |

OTHER PUBLICATIONS

Lutz; "Polymerization of Oligo(Ethylene Glycol)(Meth)Acrylates: Toward New Generations of Smart Biocompatible Materials"; Journal of Polymer Science Part A—Polymer Chemistry; vol. 46; 2008; p. 3459-3470.
Office Action issued in Japanese Application No. 2016-506343, dated Mar. 2, 2018.
Office Action issued in European Application No. 14779243.6; dated Jan. 5, 2018.
International Patent Application No. PCT/US2014/032304; Int'l Search Report and the Written Opinion; dated Aug. 15, 2014; 14 pages.
International Patent Application No. PCT/US2014/032304; Int'l Preliminary Report on Patentability; dated Mar. 6, 2015; 7 pages.
European Patent Application No. 14779243.6; Extended Search Report; dated Oct. 18, 2016; 10 pages.

*Primary Examiner* — James W Rogers
(74) *Attorney, Agent, or Firm* — BakerHostetler

(57) ABSTRACT

The invention concerns methods of removing undesirable molecules from the blood or physiologic fluid; said method comprising contacting said blood or physiologic fluid with a sorbent, said sorbent comprising a plurality of solid forms and comprising a cross-linked polymeric material having a plurality of ligands attached to the surface of said cross-linked polymeric material, comprising (i) zwitterionic moieties, (ii) oligo(ethylene glycol) moieties or (iii) mixtures thereof; said contacting comprising said sorbent sorbing a plurality of said undesirable molecules when said sorbent is administered within a patient's body.

13 Claims, No Drawings

HEMOCOMPATIBILITY MODIFIERS FOR CROSS-LINKED POLYMERIC MATERIAL

CROSS REFERENCE TO RELATED APPLICATIONS

This application is a continuation application of U.S. patent application Ser. No. 14/230,108, filed Mar. 31, 2014 and claims benefit to U.S. Provisional Application No. 61/806,990 filed Apr. 1, 2013, the disclosure of which is hereby incorporated by reference herein in its entirety.

GOVERNMENT RIGHTS

This material is based upon work supported by DARPA and SSC Pacific under Contract No. N66001-12-C-4199. Accordingly, the United States Government may have rights in the invention described herein.

TECHNICAL FIELD

The present invention concerns methods useful in one or more of increasing shelf life of the blood, blood product or physiologic fluid; maintaining freshness of new blood, blood product or physiologic fluid; and removing undesirable molecules from the blood, blood product or physiologic fluid using hemocompatibility modified cross-linked polymeric material.

BACKGROUND

The transfusion of whole blood or derivatives of whole blood ("blood products") are literally the lifeblood of patients with a range of conditions from severe trauma to surgery to cancer. According to the American Red Cross, there are more than 14 million packed red blood cell (pRBC) transfusions per year in the United States with 1 in every ten admissions to US hospitals requiring a blood transfusion on average. A similar number of transfusions of other fractions of whole blood, or blood products, such as platelets, white blood cells, plasma, albumin, immunoglobulins, clotting factors and cryoprecipitate, are administered each year. The critical need for blood extends to the military, where logistics of blood transport and storage are complicated and 8% of all hospital admissions during Operation Iraqi Freedom required massive transfusions, defined as more than 10 units of blood in the first 24 hours. Whole blood and blood products will be collectively referred to herein as "blood".

Blood has a limited life span. A typical pRBC unit has a usable life of only 42 days while platelets must be used within 5 days of donation. This, coupled with the high demand for blood, has led to periodic blood shortages. But many medical experts believe fresh blood should be used even sooner, within 2-4 weeks. Retrospective studies have implicated transfusions of "older" blood with an increased risk of non-hemolytic transfusion reactions such as fever, transfusion related acute lung injury (TRALI), transfusion associated dyspnea (TAD), allergic reactions, infection, death and other complications. In one of these studies, the risk of in-hospital death increased by 2% for each day a packed red cell unit aged. Because of this, extending the useful life of blood products and improving the quality of blood would be helpful.

Techniques of blood purification via extracorporeal therapy or transfusion related products are reliant on the hemocompatibility of materials used. In some endues, sorbents can be used in treating bacterial toxins or other toxins in the blood using a hemocompatible sorbent in an extracorporeal hemoperfusion system. Standard hemodialysis, hemofiltration and charcoal hemoperfusion techniques are limited in the toxins that they remove. Improved systems would benefit the field of use.

Activated charcoal, a pure form of carbon that is processed to be highly adsorbent of particles and gases in the body's digestive system has been used since ancient times to cure a variety of ailments including poisoning. A biocompatible and hemocompatible system with improved performance in the removal of toxins would also be beneficial to the medical profession.

SUMMARY

In some embodiments, the invention concerns methods of treating blood, blood product, plasma or physiologic fluid to provide at least one of (i) increasing shelf life of the blood, blood product or physiologic fluid, (ii) maintaining freshness of new blood, blood product or physiologic fluid, and (iii) removing undesirable molecules from the blood, blood product or physiologic fluid; the method comprising contacting the blood, blood product or physiologic fluid with a sorbent, the sorbent being primarily in a plurality of solid forms and comprising a cross-linked polymeric material having a plurality of at least one of (1) zwitterionic moieties and (2) oligo(ethylene glycol) moieties attached to the surface of the cross-linked polymeric material.

Preferred sorbents include cross-linked polymeric material derived from the reaction of a cross-linker with one or more of the following polymerizable monomers: divinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate.

In certain embodiments, the zwitterionic moieties comprise one or more carboxybetaine and sulfobetaine zwitterionic moieties. Some preferred compositions comprise at least one zwitterionic moiety of the formula

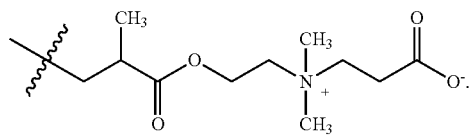

Some preferred methods comprise compositions where oligo(ethylene glycol) moieties comprise at least one group of the formula:

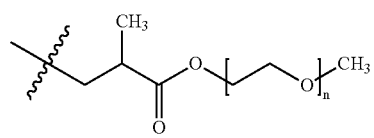

where n is an integer from 3-8.

In certain methods, the solid form is porous. Some solid forms are characterized as having a pore structure having a total volume of pore sizes in the range of from 10 Å to 10,000 Å is greater than 0.5 cc/g to 3.0 cc/g dry polymer; wherein the ratio of pore volume between 10 Å to 3,000 Å in diameter to pore volume between 500 Å to 3,000 Å in diameter of the cross-linked polymeric material is smaller than 7:1 and wherein the ratio of pore volume between 10 Å to 3,000 Å in diameter to pore volume between 10 Å to 6,000 Å in diameter of the cross-linked polymeric material is less than 2:1.

In another embodiment, polymers comprise particles having a diameter in the range for 0.1 micron meters to 2 centimeters. Certain polymers are in the form of powder, beads or other regular or irregularly shaped particulates. The pore structure of some polymers is such that the total pore volume of pore size in the range of 50 Å to 10,000 Å is greater than 0.5 cc/g to 3.0 cc/g dry polymer. In some embodiments, the polymer has a pore structure such that the total pore volume of pore size in the range of 50 Å to 10,000 Å is greater than 0.5 cc/g to 3.0 cc/g dry polymer; wherein the ratio of pore volume between 50 Å to 10,000 Å (pore diameter) to pore volume between 5001 to 3,0008 (pore diameter) of the polymer is smaller than 200:1; and the ratio of pore volume between 50 Å to 3,0008 (pore diameter) to pore volume between 1,000 Å to 3,0008 (pore diameter) of the polymer is greater than 20:1.

In some methods, the undesirable molecules are biologically active molecules (BAMs), biological response modifiers (BRMs), products of hemolysis, products of membrane or cellular degradation, toxins, drugs, antibodies, prions and similar molecules found in stored blood and blood products. In certain methods, the biologically active molecules comprise inflammatory mediators and stimulators. In some embodiments, the inflammatory mediators and stimulators comprise cytokines, nitric oxide, thromboxanes, leukotrienes, platelet-activating factor, prostaglandins, glycoproteins, kinins, kininogens, complement factors, cell-adhesion molecules, superantigens, monokines, chemokines, interferons, free radicals, proteases, arachidonic acid metabolites, prostacyclins, beta endorphins, myocardial depressant factors, anandimide, 2-arachadonylglycerol, tetrahydrobiopterin, serotonin, histamine, bradykinin, soluble CD40 ligand, bioactive lipids, oxidized lipids, hemoglobin, red cell particulates, membrane or cellular components, growth factors, glycoproteins, prions, toxins, endotoxins, drugs, vasoactive substances, foreign antigens, microvesicles and antibodies.

Preferred methods include those where the zwitterionic moieties and oligo(ethylene glycol) moieties are covalently bonded to the surface of the cross-linked polymeric material. In some embodiments, the zwitterionic moieties and oligo (ethylene glycol) moieties are covalently bound to the surface of the cross-linked polymeric material by radical polymerization of ethylenically unsaturated zwitterionic monomers having a sulphobetaine group with an unsaturated group residing on the surface of the cross-linked polymeric material.

The methods of the invention can be performed such that the sorbent sorbs in vivo or ex vivo. In certain methods, the sorbent is contained within a compliant container suitable for the storage of blood, blood products or physiologic fluid and the sorbent being substantially free-flowing within the compliant container. In other methods, the is ingested or rectally administered within the human body. In some embodiments, the method is part of an extra corporeal treatment.

In some embodiments, the plurality of solid forms comprises particles having a diameter in the range for 0.1 micron meters to 2 centimeters.

The invention also concerns blood filtration devices comprising a filter cartridge comprising a sorbent, the sorbent being primarily in a plurality of solid forms comprising particles having a diameter in the range for 0.1 micron meters to 2 centimeters; the sorbent comprising a cross-linked polymeric material having a plurality of at least one of (1) zwitterionic moieties and (2) oligo(ethylene glycol) moieties attached to the surface of the cross-linked polymeric material.

Preferred sorbents include cross-linked polymeric material derived from the reaction of a cross-linker with one or more of the following polymerizable monomers: divinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate.

Preferred sorbents are biocompatible and hemocompatible.

In certain embodiments, the zwitterionic moieties comprise one or more carboxybetaine and sulfobetaine zwitterionic moieties. Some preferred compositions comprise at least one zwitterionic moiety of the formula

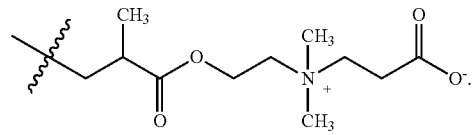

Some preferred devices comprise compositions where oligo(ethylene glycol) moieties comprise at least one group of the formula:

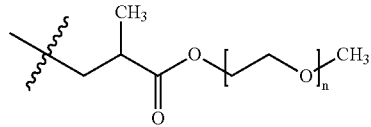

where n is an integer from 3-8.

In certain devices, the solid form is porous. Some solid forms are characterized as having a pore structure having a total volume of pore sizes in the range of from 10 Å to 10,000 Å is greater than 0.5 cc/g to 3.0 cc/g dry polymer; wherein the ratio of pore volume between 10 Å to 3,000 Å in diameter to pore volume between 500 Å to 3,000 Å in diameter of the cross-linked polymeric material is smaller than 7:1 and wherein the ratio of pore volume between 10 Å to 3,000 Å in diameter to pore volume between 10 Å to 6,000 Å in diameter of the cross-linked polymeric material is less than 2:1.

In some embodiments, the blood filtration devices contain particles described herein that are free-flowing within the filter cartridge. Filter cartridges can be made from any suitable material and in any suitable configuration, including those known in the art.

In additional embodiments, the invention concerns use of a sorbent described herein within a compliant container suitable for the storage of blood, blood product or physiologic fluid.

DETAILED DESCRIPTION OF ILLUSTRATIVE EMBODIMENTS

The present invention seeks to apply a zwitterionic coating to porous styrene/divinylbenzene (ST/DVB) co-polymer resins in order to produce a material that has blood purification properties but is also hemocompatable and non-thrombogenic in both high and low-flow rate situations.

Poly(ethylene glycol) (PEG) is the current standard for achieving protein stabilization and increasing body circulation times for synthetic biomaterials. However, PEGylation is also known to reduce the binding affinity of a material, thereby mitigating its bioactivity. Therefore PEGylation of a material might be an appropriate route if one wishes to achieve bioinvisibilty of a material, but if the material must be biocompatible while also displaying certain selective bioactivity; superior technologies remain to be realized.

A family of ultra-low fouling, biocompatible, zwitterionic polymers have been developed and have demonstrated potential utility in applications ranging from blood-contacting devices and implanted biomaterials to surface based diagnostic devices. The zwitterionic polymers of interest are poly(sulfobetaine) and poly(carboxybetaine) (Scheme 1).

We envision producing methacrylate derivatives of the betaine monomers. These monomers are sulfobetaine methacrylate (Scheme 1a) and carboxybetaine methacrylate (Scheme. 1b). The alkene functionality of the methacrylate will allow the zwitterionic monomer to be grafted on to the surface of our ST/DVB copolymer resin via free radical polymerization.

Scheme 1 a.

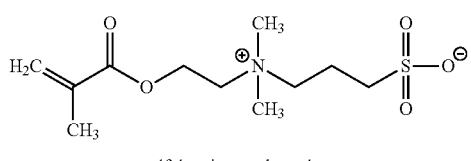

sulfobetaine methacrylate b.

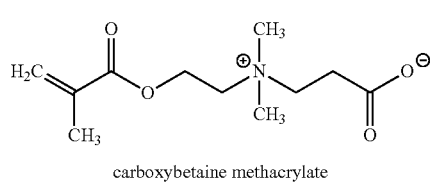

carboxybetaine methacrylate

Other possible monomers include betaines and ylides. Non-limiting examples of suitable betaine monomers include: N-(2-hydroxy-3-sulfopropyl) vinyl pyridinium betaine, N,N-dimethyl-N-(2-methacryoyloxyethyl)-N-(3-sulfopropyl) ammonium betaine, N,N-dimethyl-N-(3-methyacrylamidopropyl)-N-(3-sulfopropyl) ammonium betaine, N,N-dimethyl-N-(2-methacryloyloxyethyl)-N-(carboxymethyl) ammonium betaine, N,N-dimethyl-N-(2-methyacryloyloxyethyl)-N-(2-phosphoethyl) ammonium betaine.

Other possible zwitterionic moieties that may be bound to the surface through grafting or entanglement are amino acids e.g. (21 essential amino acids) either as monomeric or polymeric forms. Another possible zwitterion is 2-methacryloyloxyethyl phosphorylcholine (Scheme 2).

Scheme 2

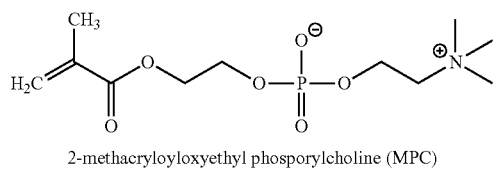

2-methacryloyloxyethyl phosporylcholine (MPC)

Alternatively, oligo (ethylene glycol) methacrylate (OEGMA) could be used as a hemocompatiblizing surface modifier (Scheme 3).

Scheme 3

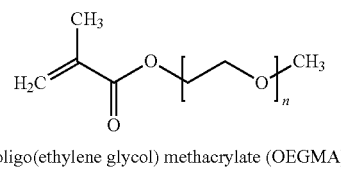

oligo(ethylene glycol) methacrylate (OEGMA)
average n = 6

The coating on the porous ST/DVB copolymer resin will imbue the material with improved hemocompatabilty and non-thrombogeneity. These zwitterions are very hydrophilic, and will give the resin beads non-fouling properties through strong ionic interactions with water. When the zwitterionic polymer is introduced to an aqueous biological system, such as blood, the surface will become extremely hydrophilic [Jiang Nat. Chem. 2011]. The water saturated surface of the polymer should provide a sufficient buffer to prevent biological fouling but should also leave enough steric space around the pores of the polymer to allow it to participate in the size-exclusion filtration and purification of blood. Since the invention relies on creating a buffer of water, rather than a synthetic material, around the device, it should be stable enough to be used at low-flow rate as well as high-flow rate.

Some preferred polymers comprise residues from one or more monomers or containing monomers or mixtures there of selected from divinylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, and divinylformamide.

In some embodiments, the polymer is a coated polymer comprising at least one crosslinking agent and at least one dispersing agent. The dispersing agent may be hemocompatible. The dispersing agents can be selected from chemicals, compounds or materials such as hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof; the cross-linking agent selected from a group consisting of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof. Preferably, the polymer is developed simultaneously with the formation of the coating, wherein the dispersing agent is chemically bound to the surface of the polymer.

Some embodiments of the invention use an organic solvent and/or polymeric porogen as the porogen or pore-former, and the resulting phase separation induced during polymerization yield porous polymers. Some preferred porogens are benzyl alcohol, cyclohexane, cyclohexanol, cyclohexanol/toluene mixtures, cyclohexanone, decane, decane/toluene mixtures, di-2-ethylhexylphosphoric acid, di-2-ethylhexyl phthalate, 2-ethyl-1-hexanoic acid, 2-ethyl-1-hexanol, 2-ethyl-1-hexanol/n-heptane mixtures, 2-ethyl-1-hexanol/toluene mixtures, isoamyl alcohol, n-heptane, n-heptane/ethylacetate, n-heptane/isoamyl acetate, n-heptane/tetraline mixtures, n-heptane/toluene mixtures, n-hexane/toluene mixtures, pentanol, poly(styrene-co-methyl methacrylate)/dibutyl phthalate, polystyrene/2-ethyl-1-hexanol mixtures, polystyrene/dibutyl phthalate, polystyrene/n-hexane mixtures, polystyrene/toluene mixtures, toluene, tri-n-butylphosphate, 1,2,3-trichloropropane/ 2-ethyl-1-hexanol mixtures, 2,2,4-trimethyl pentane (isooctane), trimethyl pentane/toluene mixtures, poly(propylene glycol)/toluene mixtures poly(propylene glycol)/cyclohexanol mixtures, and poly(propylene glycol)/2-ethyl-1-hexanol mixtures.

In some embodiments, the invention can be used to enhance extracorporeal therapy or transfusion related products that rely on hemocompatible polymeric materials to remove undesirable impurities from blood, blood products or physiologic fluids. In some endues, sorbents can be used in treating bacterial toxins or other toxins in the blood using a hemocompatible sorbent in an extracorporeal hemoperfusion system. Standard hemodialysis, hemofiltration and charcoal hemoperfusion techniques are limited in the toxins that they remove.

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

EXAMPLES

Example 1: Carboxybetaine Methacrylate (CBMA) Coated Polymer

A 500 ml resin kettle is fitted with water cooled condenser, thermocouple, bubbler, and magnetic stir bar. A gasket is installed between the top lid and bottom kettle. All unused ports are capped with the appropriate plug. Temperature is controlled with a heating mantle regulated by a temperature controller fitted with the above thermocouple and the entire apparatus is placed on a magnetic stir plate.

All reagents were ordered from Sigma-Aldrich and were used without further purification.

To the resin kettle was added hydroquinone (0.038 g) followed by a 76% solution of acrylic acid in ultrapure $H_2O$ (10.0 g). The mixture was stirred until all hydroquinone was dissolved and then N,N-dimethylaminomethacrylate (16.52 g) was added dropwise via syringe. The reaction was exothermic, heating the mixture to 50° C. and evolving a white gas. The reaction was heated to 70° C. for 4 hours. Over the course of the reaction, the mixture turned from water white to ever-darkening shades of pink.

After 4 hours, the heat was turned off, the magnetic stir bar was removed and a multi-level stir blade was installed and mounted to an overhead stir motor. The reactor was then charged with a divinylbenzene porous resin, CY12018 (100-144), (250 ml) in $H_2O$ (250 ml). The mixture was stirred at 100 RPM and heated to 80° C. for 30 minutes. Ammonium persulfate (3.00 g) was added to the reaction mixture and was allowed to stir at 80° C. for 16 h.

After cooling, the solvent is siphoned out to bead level. Reactor is filled to mark with RT water and heated to 70° C. and stirred for 30 minutes, allowed to settle for 3 to 5 minutes and then siphoned out to bead level. Beads are washed 5 times in this manner. The beads are then steam stripped for 8 hours (DRC-108-092). After steam stripping the beads are water washed 5 times and then the water is exchanged for normal saline until the osmolality reaches at least 280.

(uPTT was tested via ASTM F2382 standard test method for assessment and was found to be 102% of negative control, putting it in the uPTT category of non-activator). (62.1% to be 105% of negative control, putting it in the uPTT category of non-activator). (80.2% Cytochrome C removed, static non-competitive) (5.8% Human Serum Albumin removed, static non-competitive) (ESCA surface C, 86.3; N, 1.8; O, 11.6)

Example 2: Oligo (Ethylene Glycol) Methacrylate (OEGMA) Coated Polymer

A 500 ml resin kettle is fitted with water cooled condenser, thermocouple, bubbler, and a multi-level stir-blade. A gasket is installed between the top lid and bottom kettle. All unused ports are capped with the appropriate plug. Temperature is controlled with a heating mantle regulated by a temperature controller fitted with the above thermocouple.

The reactor was then charged with divinylbenzene porous resin, CY12018 (100-144), (200 ml), in $H_2O$ (200 ml), OEGMA (6.0 g) and is heated to 80° C. and stirred for 30 minutes at which point ammonium persulfate (2.0 g) is added. The reaction is allowed to stir for 16 hours at 80° C.

After cooling, the solvent is siphoned out to bead level. Reactor is filled to mark with RT water and heated to 70° C. and stirred for 30 minutes, allowed to settle for 3 to 5 minutes and then siphoned out to bead level. Beads are washed 5 times in this manner. The beads are then steam stripped for 8 hours (DRC-108-095). After steam stripping the beads are water washed 5 times and then the water is exchanged for normal saline until the osmolality reaches at least 280.

(uPTT was tested via ASTM F2382 standard test method for assessment and was found to be 105% of negative control, putting it in the uPTT category of non-activator). (80.2% Cytochrome C removed, static non-competitive) (6.6% Human Serum Albumin removed, static non-competitive) (ESCA surface C, 86.3; N. 0.1; O, 13.6)

Example 3: Additional Polymer Coatings

Example 1 is repeated using one or more of sulfobetaine methacrylate, N-(2-hydroxy-3-sulfopropyl) vinyl pyridinium betaine, N,N-dimethyl-N-(2-methacryoyloxyethyl)-N-(3-sulfopropyl) ammonium betaine, N,N-dimethyl-N-(3-methyacrylamidopropyl)-N-(3-sulfopropyl) ammonium betaine, N,N-dimethyl-N-(2-methacryloyloxyethyl)-N-(carboxymethyl) ammonium betaine, N,N-dimethyl-N-(2-methyacryloyloxyethyl)-N-(2-phosphoethyl) ammonium betaine as monomers and 2-methacryloyloxyethyl phosphorylcholine.

Example 4: Additional Cross-Linked Polymers

Examples 1-3 are repeated using cross-linked polymers comprising residues from one or more monomers or containing monomers or mixtures there of selected from divinylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, and divinylformamide. Various cross-linking and dispersing agents may be used as described herein.

Example 5: Sorbent Synthesis

Reactor Setup, A jacketed kettle (5 L) is fitted with an overhead stirrer, baffle, multi-level stirrer blade, water cooled condenser, thermocouple, bubbler and gaskets (where appropriate). All unused ports are capped with the appropriate plug. Temperature is controlled with a heating/cooling unit with the temperature controller fitted with the above thermocouple.

Polymerization, The Polyvinyl Alcohol is dispersed in the water charge at room temperature (RT) and then heated to 70° C. The remaining salts (See Table 1, MSP, DSP, TSP, & Sodium Nitrite) are then dissolved in the water charge. The PVA and Salts solutions are heated to 80° C. with stirring. The pre-mixed organic phase including the initiator is poured into the reactor onto the aqueous phase with the stirring speed set at the rpm for formation of the appropriate droplet size. Once temperature reaches 80° C. start reaction timer (16 hours).

TABLE 1

| Aqueous Phase Charges | |
|---|---|
| Item | Charge, g |
| Ultrapure Water | 1734.47 |
| Polyvinyl Alcohol (PVA) | 5.06 |
| Monosodium Phosphate (MSP) | 5.34 |
| Disodium Phosphate (DSP) | 17.71 |
| Trisodium Phosphate (TSP) | 10.99 |
| Sodium Nitrite | 0.05 |
| Total | 1773.63 |
| Organic Phase Charges | |
| Item | Charge, g |
| Divinylbenzene (DVB) (63%, Deltech Corp.) | 592.92 |
| Toluene | 390.48 |
| Isooctane | 448.47 |
| Benzoyl Peroxide (BPO) (97%) | 4.49 |
| Total, w/o BPO | 1431.87 |

Work-up Mark solvent level. After cooling the solvent is siphoned out to bead level. Reactor is filled to mark with (RT) water and heated to 50° C. to 70° C. and stirred for 30 minutes, allowed to settle for 3 to 5 minutes and then siphoned out to bead level. Beads are washed 5 times in this manner. The polymer is steam stripped 6 hours and then dried in an oven overnight (~100° C.). This process results in a clean, dry porous sorbent in the form of spherical, divinylbenzene porous polymer beads. The beads were rewet with 70% IPA and the IPA exchanged with water for further reactions under aqueous conditions.

Example 6: Pore Structure Characterization

The pore structures of the sorbent polymers are analyzed with a either Micromeritics AutoPore IV 9500 V1.09 a Mercury Penetrometer (Hg Intrusion instrument) or a Micromeritics ASAP 2010 instrument (N2 Desorbtion).

Example 7: Blood Filtration Device

The coated polymers of examples 1-3 are placed in a cartridge suitable for blood filtration.

Example 8: Blood Storage Bag

The coated polymers of examples 1-3 are placed in a storage bag suitable for blood or blood product.

What is claimed:
1. A method of removing undesirable molecules from physiologic fluid; said method comprising contacting said physiologic fluid with a sorbent, said sorbent comprising a plurality of solid forms and comprising a cross-linked polymeric material having a plurality of ligands attached to the surface of said cross-linked polymeric material, said ligands comprising zwitterionic moieties;
wherein the sorbent is administered orally or rectally;
wherein said sorbent comprises particles having a diameter in the range for 0.1 micron meters to 2 centimeters,
wherein said particles are characterized as having a pore structure having a total volume of pore sizes in the range of from 10 Å to 10,000 Å that is between (a) greater than 0.5 cc/g dry polymer and (b) 3.0 cc/g dry polymer;

wherein said sorbent comprises cross-linked polymeric material derived from the reaction of a cross-linker with one or more of the following polymerizable monomers: divinyl-benzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate; and wherein said zwitterionic moieties comprise one or more carboxybetaine and sulfobetaine zwitterionic moieties.

2. The method of claim 1, wherein said zwitterionic moieties comprise at least one residue of carboxybetaine methacrylate.

3. The method of claim 1, wherein said zwitterionic moieties comprise at least one group of the formula

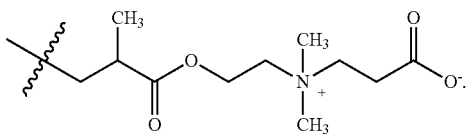

4. The method of claim 1, wherein said undesirable molecules are biologically active molecules (BAMs), biological response modifiers (BRMs), products of hemolysis, products of membrane or cellular degradation, toxins, drugs, antibodies, prions and similar molecules found in stored blood and blood products.

5. The method of claim 4, wherein the biologically active molecules comprise inflammatory mediators and stimulators.

6. The method of claim 5, wherein said inflammatory mediators and stimulators comprise cytokines, nitric oxide, thromboxanes, leukotrienes, platelet-activating factor, prostaglandins, glycoproteins, kinins, kininogens, complement factors, cell-adhesion molecules, superantigens, monokines, chemokines, interferons, free radicals, proteases, arachidonic acid metabolites, prostacyclins, beta endorphins, myocardial depressant factors, anandimide, 2-arachadonylglycerol, tetrahydrobiopterin, serotonin, histamine, bradykinin, soluble CD40 ligand, bioactive lipids, oxidized lipids, hemoglobin, red cell particulates, membrane or cellular components, growth factors, glycoproteins, prions, toxins, endotoxins, drugs, vasoactive substances, foreign antigens, microvesicles and antibodies.

7. The method of claim 4, where undesirable molecules are antibodies.

8. The method of claim 1, wherein said zwitterionic moieties are covalently bonded to the surface of said cross-linked polymeric material.

9. The method of claim 1, wherein said zwitterionic moieties are covalently bound to the surface of said cross-linked polymeric material by radical polymerization of ethylenically unsaturated zwitterionic monomers having a sulphobetaine group with an unsaturated group residing on the surface of said cross-linked polymeric material.

10. The method of claim 1, wherein said sorbent is a biocompatible polymer.

11. The method of claim 1, wherein said polymer is hemocompatible.

12. The method of claim 1, wherein said sorbent comprises cross-linked polymeric material derived from the reaction of a cross-linker with one or more of the following polymerizable monomers: divinyl-benzene, styrene, and ethylstyrene.

13. The method of claim 1, wherein the ratio of pore volume between 10 Å to 3,000 Å in diameter to pore volume between 500 Å to 3,000 Å in diameter of the said cross-linked polymeric material is smaller than 7:1 and wherein the ratio of pore volume between 10 Å to 3,000 Å in diameter to pore volume between 10 Å to 6,000 Å in diameter of said cross-linked polymeric material is less than 2:1.

* * * * *